US00PP09098P

United States Patent [19]

Milbrath et al.

[11] Patent Number: Plant 9,098

[45] Date of Patent: Apr. 4, 1995

[54] BLUEBERRY: CRYSTAL BLUE

[76] Inventors: Cyril M. Milbrath, 5591 Hwy. 194, Hermantown, Minn. 55811; Cecil Stushnoff, 7309 Didrickson Ct., Fort Collins, Colo. 80525

[21] Appl. No.: 172,639

[22] Filed: Dec. 22, 1993

[51] Int. Cl.[6] ..... A01H 5/00

[52] U.S. Cl. ..... Plt./33.1

[58] Field of Search ..... Plt. 33.1

*Primary Examiner*—James R. Feyrer

*Attorney, Agent, or Firm*—Merchant, Gould, Smith, Edell, Welter & Schmidt

[57] ABSTRACT

A new and distinct variety of blueberry characterized by winter hardiness, spring flower bud hardiness, and high quality medium sized fruit.

3 Drawing Sheets

BACKGROUND INFORMATION

The present invention relates to a new and distinct cultivar of blueberry, which is cold-hardy and low-statured and presents a combination of unique characteristics. This new variety originated from a hand pollinated, interspecific hybridization of Minnesota Selection B-6×Minnesota Selection 69-3, which was made by inventor Cecil Stushnoff in 1969 at the Horticultural Research Center of the University of Minnesota, located near Excelsior, Minn.

The seeds resulting from such hybridization were germinated in 1969 and the resulting seedlings were planted in the spring of 1971 in a field research plot of the University of Minnesota located near Elk River, Minn. In 1975, several thousand of such seedlings were moved from the Elk River, Minn. site to other experimental sites in Minnesota, for further testing. The seedling which was subsequently selected as the present variety was one of a large number of such seedlings assigned to co-operator and co-inventor Cy Milbrath, for further testing at his nursery located in northern Minnesota. Such nursery is known as Marcy Blueberry Nursery and is located on the shore of Crystal Lake, approximately 16 miles south of Virginia, Minn. Specifically, such nursery is ⅛ mile west of U.S. Highway 53 on County Road 621, in St. Louis County. Following several years of over-wintering and summer fruiting, the superior performance characteristics of the present variety compared to other named cultivars and numerous other seedlings derived from the above-noted hybridization, including lack of winter injury, were recognized by the co-inventors named herein, and in 1978 the seedling of this variety was identified as M-30.

The original selection of the present variety, designated M-30, has been propagated asexually by the rooting of softwood cuttings, and a test planting of seventeen plants was established at the above-noted nursery of Cy Milbrath. The original plant of the present variety has been observed each year for the past 18 years, and since 1975 data has been collected on winter injury relative to meteorological climatic conditions.

This new variety has demonstrated superior performance with respect to two important characteristics of cold hardiness, which are mid-winter survival and spring flower bud hardiness. Mid-winter survival of this new variety is evident from both exposure to severe freezing events during the past 18 years at the above-noted northern Minnesota location adjacent Crystal Lake, Minn., as well as from controlled freezing tests made under laboratory conditions.

The above-noted Crystal Lake, Minn. test site at the nursery of co-inventor Cy Milbrath is located in USDA winter hardiness map zone 3a, where minimum temperatures attain −35° F. as determined by 35 year temperature records. A low temperature of −45° F. was recorded Dec. 31, 1976, at Virgina, Minn., which is approximately 16 miles north of the test site at Crystal Lake, Minn. It is therefore likely that the original test plant has been exposed to at least −40° F. and has survived 18 years at the test site located near Crystal Lake, Eveleth, Minn. Controlled freezing tests have shown survival of stems frozen at −8° F. per hour, down to −40° F., and survival of flower buds down to −25° F.

Blueberry plants are typically of the low-bush or high-bush variety. The low-bush types have good fruit flavor and usually have fruit set because the low plant stature normally is covered by snow. The high-bush types normally have higher fruit production but the berry flavor may not be as desirable and the plants are generally not as winter hardy. This new variety has the fruit flavor characteristic of the low bush types, but with the increased fruit production of the high-bush types, and the variety also has considerable winter hardiness.

One of the problems with respect to the blueberry hardiness is survival of flower buds during below-freezing periods in the spring. On Apr. 29, 1990, the flower buds on plants of this variety survived a temperature of 22° F., as well as a temperature of 23° F. on Apr. 30, 1990, at the above-noted nursery test site at Crystal Lake, Eveleth, Minn., and later that summer produced a crop of fruit. With such frost conditions on Apr. 29–30, 1990, all other selections and cultivars of blueberry plants located at the nursery test site at Crystal Lake, Eveleth, Minn. experienced flower bud damage, and none thereof produced any fruit that year.

The plants of this new variety are erect and moderately vigorous for low-statured blueberry plants. Plants of this variety attain a height of 80 cm after three years and 95 cm at maturity. Two to three new shoots emerge from the base of the plants each year, but the narrowness and openness of the plant indicates that the present variety may likely be suitable for mechanical harvesting of fruit. The new growth of stems is light green in color, changing to crimson in the autumn. New growth may be distinguished by its pubescent (fuzzy) texture of the stems. The pubescence remains on the stems and appears to be a distinguishing feature as compared to other varieties of blueberries observed by the inventors. The leaves are dark green to blue-green in color and 20–25 mm wide and 40–50 mm in length.

Lateral flower buds form on first year shoot growth. The flowers are white with 6–8 flowers per cluster. Flowering occurs from the 3rd week in May through the 2nd week in June at the above-noted test site near Crystal Lake, Eveleth, Minn. It has also been observed that the new flower buds which form in the autumn tend to curl or close up in late fall.

With respect to berry production, the berries begin maturation for harvest about the third week in July and may be harvested until mid-August, at the above-noted nursery test site at Crystal Lake, Eveleth, Minn. The berries of this new variety are similiar in size to large low-bush blueberries, range from 5 mm to 13 mm in diameter, and average 6 mm×9 mm in size. A light bloom covers the medium blue colored berries, which have a small dry scar. The berries are medium to firm and resemble the fruit on low-bush blueberry plants, and during normal seasons it is believed that this new variety may be suitable for mechanical harvesting of fruit.

The berries on this new variety are highly flavored, similar to low-bush blueberries, and posssess a good balance of sugar to acid, have normal skin thickness and small seeds. Fruit of this variety which has been frozen, has stored very well.

This new variety has exhibited no evidence of infestation of common blueberry diseases, such as stem blight, cane canker and witches broom, but precise levels of resistance to diseases will require more observation and testing.

The combination of characteristics of this new variety which are believed to be unique include winter hardiness, spring flower bud hardiness, medium berry size, low leaf density, the open structure of the lower plant branches which permits access to berries and possible mechanical harvesting of fruit, generally heavy fruit set, the manner in which the flower buds close up in autumn and the flavor and quality of the berries.

DESCRIPTION OF THE DRAWINGS

This new variety of blueberry is illustrated by the accompanying photographic drawings.

PLANT PEDIGREE

Figure 1:
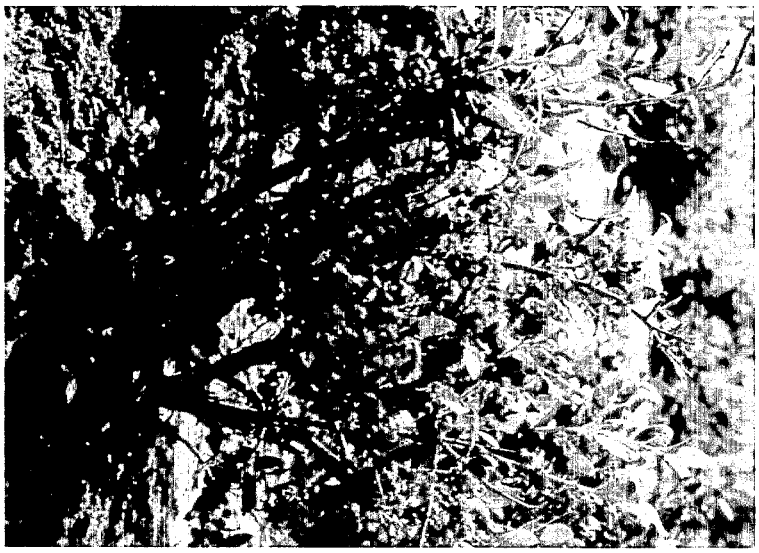
FIG. 1 is a photographic print in full color of an entire plant and showing the open nature of the lower portion of the plant.
Figure 2:
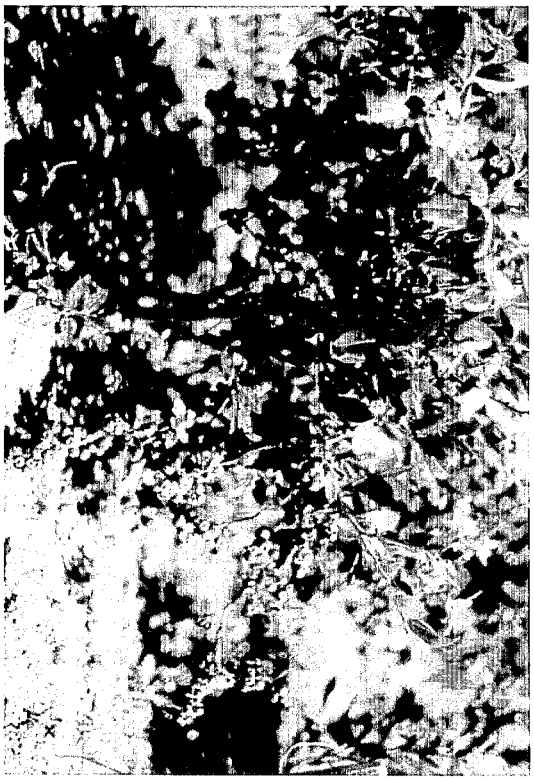
FIG. 2 is a photographic print in full color of an entire plant showing fruit set.
Figure 3:
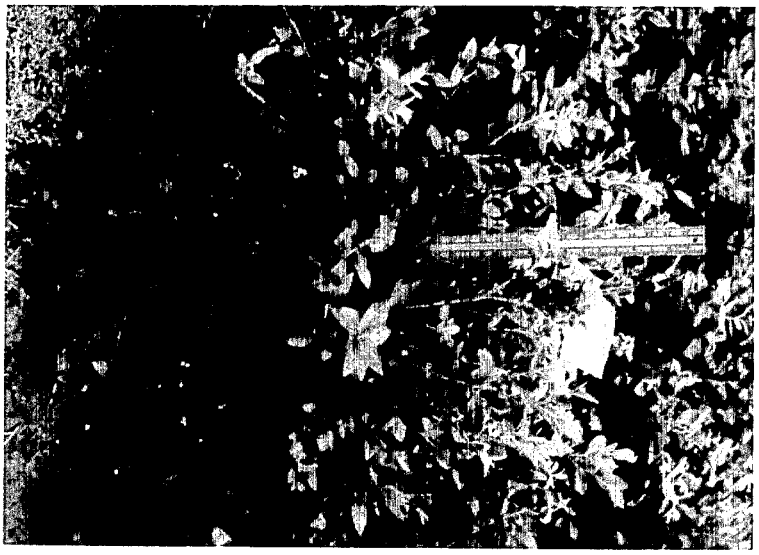
FIG. 3 is a full color photographic print of an entire plant showing mature plant height.
Figure 4:
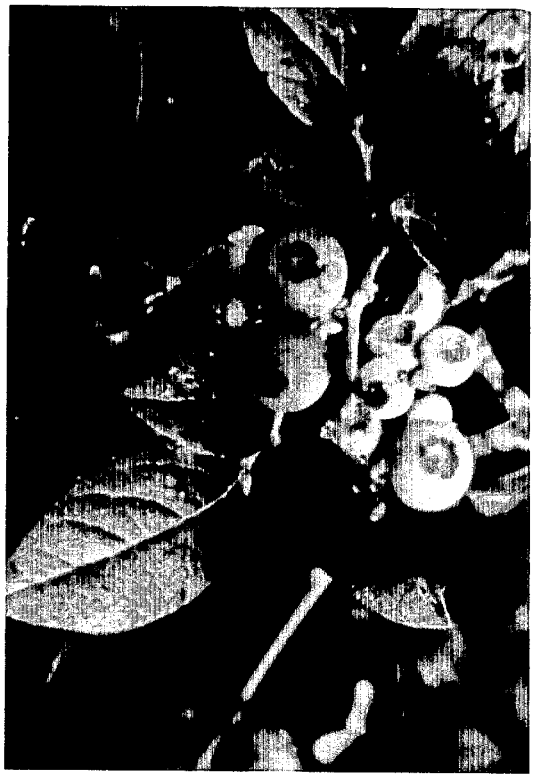
FIG. 4 is a full color phoitographic print illustrating fruit clusters.
Figure 5:
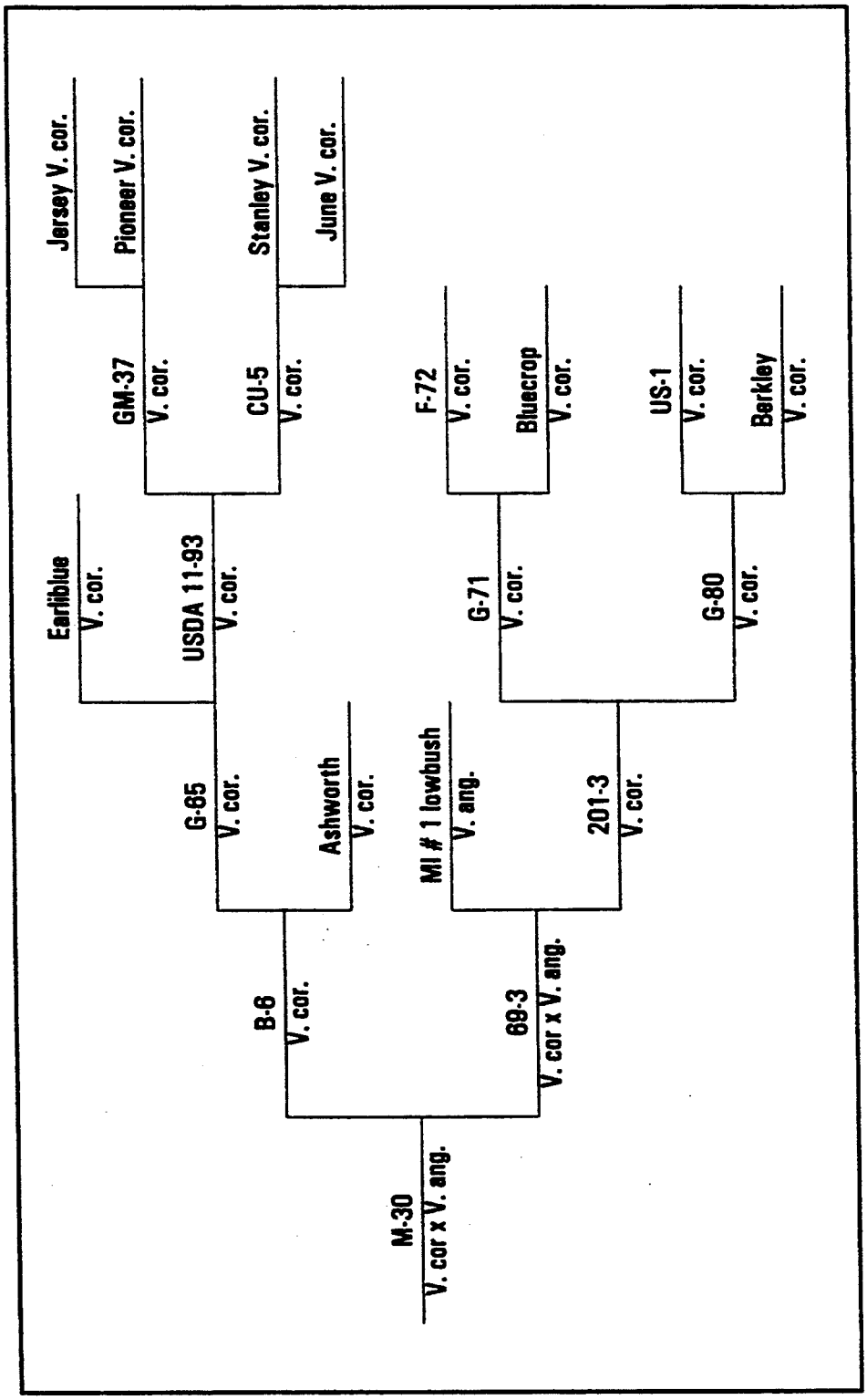
FIG. 5 is a chart showing the pedigree of the plant of this disclosure.

The pedigree of this new variety is depicted in FIG. 5. The species of each of the parent plants is indicated as follows: *V. cor.* = *Vaccinium corymbosum* L.; and *V. ang.* = *Vaccinium angustifolium* Aiton.

DETAILED PLANT DESCRIPTION

The following is a detailed description of the pomological characteristics of this new variety. Where dimensions, sizes, and colors are given, it is to be understood that such characteristics are approximations of averages set forth as accurately as practicable. The description is based on observation of specimens grown in Crystal Lake, Eveleth, Minn. at the nursery of co-inventor Cy Milbrath, where softwood cuttings of the variety have been rooted. The color determinations and comparisons are based on the Horticultural Colour Chart published by the British Colour Council in collaboration with The Royal Horticultural Society, Volume II published in 1942.

Plant:

*Size.*—Low statured, 90 cm tall with about 10 shoots sprouting from a base 25–30 cm wide from a mature 5 year old plant.

*Time of* 50% *anthesis.*—May 25.

*Growth.*—Medium to high vigor, cessation of growth early September, plant erect.

*Productivity.*—Consistent from season to season.

*Cold hardiness.*—Outstanding for an erect plant. The stems have consistently survived 40° C., mid-winter flower buds −30° C. and spring buds and flowers −5° C.

*Chilling requirements.*—Unknown.

*Stems.*—Erect, 2–3 new pubescent shoots each year with up to 50–60 cm growth in the first year and 80–90 cm by the third year. Shoot growth from upper lateral buds average 6.5 cm per year.

*Internode length.*—1.5 cm. Dormant twigs are dark pink to red in color. Vol II, Chrysanthemum Crimson, Plate 824/2.

*Disease resistance.*—No evidence of stem blight and cane canker, good resistance to witches broom.

Foliage:

*Leaves.*—Color—Mature leaves dark green to blue green, Vol. II, Parsley Green, Plate 00962/1. Color of underside of leaf — Greyed green, RHS London, Fan 4, greyed-green group 191, color B. Glabrous, 20–25 mm wide×40–50 mm long.

*Leaf stem.*—Round, 33 mm long, Color — pale pink.

Flowers:

*Date of* 50% *anthesis.*—May 25.

*Flower color.*—White.

*Flower shape.*—Urceolate, mean corolla length: 7 mm: width 5 mm: mean diameter of corolla tube aperture 3 mm.

*Flower bud number.*—6–8 florets per bud.

Fruit:

*Maturity.*—First harvest July 20, last harvest August 15.

*Size of berry.*—Medium-small, average berry dimensions 6×9 mm, calyx cup 2 mm deep.

*Berry color.*—Medium blue with a light bloom. Vol. II, Butterfly Blue, Plate 645/1.

*Fruit stem scar.*—Small and dry.

*Berry firmness.*—Medium to firm.

*Berry flavor and texture.*—Distinct wild blueberry flavor with good sugar to acid balance.

*Shoot productivity.*—Up to seven years. With the passage of time (5–7 years), regular pruning is suggested every 2 to 3 years to obtain optimum production and fruit size.

*Storage quality.*—Medium.

*Uses.*—A cold hardy blueberry for short season, northern regions experiencing very cold winters. The high quality berries resemble low bush blueberry fruit and the variety is believed suitable for commercial berry production and for home gardening use.

Distinctiveness: The most distinctive feature is very good cold hardiness for an erect plant. The long-term, 18 year record of survival provides evidence of its resistance to cold stress. The highly flavored berries are believed suitable for customer-pick local markets and home gardening in northern regions.

I claim:

1. A new and distinct variety of cold hardy blueberry plant, substantially as illustrated and described, characterized by high quality medium sized fruit, with plants adapted to short growing seasons and very high resistance to winter injury from freezing stresses.

* * * * *